United States Patent [19]

Catalano

[11] Patent Number: 4,610,252
[45] Date of Patent: Sep. 9, 1986

[54] DUAL MUSCLE CLAMP

[76] Inventor: J. Denis Catalano, 609 Claymont Estates Dr., Ballwin, Mo. 63011

[21] Appl. No.: 660,631

[22] Filed: Oct. 15, 1984

[51] Int. Cl.$^4$ ............................................. A61B 17/00
[52] U.S. Cl. .................................................... 128/346
[58] Field of Search ............... 128/346, 354, 321, 322, 128/318

[56] References Cited

U.S. PATENT DOCUMENTS

| | | | |
|---|---|---|---|
| 2,504,202 | 4/1950 | Kadavy | 128/354 |
| 2,668,538 | 2/1954 | Baker | 128/346 |
| 3,809,094 | 5/1974 | Cook | 128/346 |
| 4,165,748 | 8/1979 | Heifetz | 128/354 |

Primary Examiner—Robert Peshock
Attorney, Agent, or Firm—Haverstock, Garrett & Roberts

[57] ABSTRACT

A dual muscle clamp used in ocular surgery. Two pairs of spaced jaws are connected to a dual element handle. The handle elements are pivotally connected together to move the jaws between clamping and spread conditions to clamp and release tissue. Spring portions on the handle elements bias the jaws to the spread condition. A spring biased hook on one handle element interlinks with the edge of an opening on the other handle element to latch the jaws in the clamping condition. Opposed pointed teeth on the jaws interfit in the clamped condition and pierce the tissue clamped between the jaws. Semi-cylindrical portions on the handle elements cooperatively define a cylinder for comfortable gripping and careful and precise control with a single hand.

12 Claims, 12 Drawing Figures 4,610,252

DUAL MUSCLE CLAMP

BACKGROUND OF THE INVENTION

This invention relates to a muscle clamp and particularly a muscle clamp used in ocular surgery to hold an eye during surgery to correct a strabismus condition.

Strabismus is caused by lack of coordination of movement of the eyes. Movement of the eyes is controlled by eye muscles. Sometimes these eye muscles do not work together and the eyes may be non-synchronized in their movements. If the condition is severe, surgery to either shorten or lengthen an eye muscle may be necessary. To perform this surgery, the eye muscle must be severed from the eye and then re-attached at a different point. After the muscle has been cut, the eye must be held so the eye muscle can be re-attached at a precise location. A muscle clamp is used to rotate and move the eye to a desired position and then hold the eye stationary in that position during the surgery.

Muscle clamps have been used in the past in ocular surgery. These muscle clamps typically consist of a single pair of tiny jaws that can be moved together to clamp the schlera tissue of an eyeball and can be separated to release the tissue. The problem with these typical muscle clamps is that a single clamp does not afford enough control and leverage to rotate and move an eye to a precise position and hold it there. During a suturing operation, it is necessary for the eye to be held in such a way that the surgeon can attach an entire edge of the muscle to the eyeball. Therefore, using the existing muscle clamps, two such muscle clamps are required, to be clamped to the schlera at spaced points. Each muscle clamp must be held in a separate hand. Therefore, since one of the surgeon's hands must handle the suture needle or its holder, he has only one free hand and an assistant is required. The assistant must use both hands, one for each muscle clamp. This means the assistant does not have a free hand for doing other helpful work.

Also, there may be times when the surgeon would prefer or would be required to handle the muscle clamp himself and if so, in the present state of the art, he must make both of his hands available. An advantage of the present invention is that it provides a dual jaw muscle clamp that clamps and holds the tissue at two spaced points and that can be held in one hand.

An object of the present invention is to provide a dual muscle clamp having two separate pairs of jaws that work together to clamp tissue, such as the schlera of an eye, at spaced points. Pursuant to this object, the muscle clamp of the present invention can be handled with one hand and the one hand can manipulate both of the pairs of clamping jaws simultaneously to precisely position the clamped eyeball. Accordingly, another object of the invention is to provide a dual muscle clamp for use in ocular surgery wherein the clamping can be accomplished with only one hand thereby enabling the surgeon to handle the muscle clamp himself while the surgeon's other hand is handling a suturing needle or a needle holder; or thereby requiring only one hand of an assistant to handle the clamping means.

Another problem with the prior art muscle clamps is that the handles by which they are held are not comfortable or are awkward or have only one or two ways in which they can be comfortably and conveniently held. These restrictions limit the maneuverability of the muscle clamp to precisely locate the muscle clamping jaws. An object of the present invention is to provide a dual muscle clamp that has a handle that is comfortable to hold and that enables precise maneuvering of the muscle clamp. Specifically, an object of the present invention is to provide a dual muscle clamp with a cylindrical handle, the handle being substantially similar in diameter to the diameter of a mechanical pencil, the length of the handle being such that a portion of it can be gripped within the thumb and first two fingers of the hand and the rearward portion of the handle will rest against the hypothenar space of the hand.

Another important object of the invention is to provide a dual muscle clamp with a handle that is substantially identical to the handle on other surgical instruments used by the surgeon in sequence in the course of a single surgical operation.

SUMMARY OF THE INVENTION

This invention is directed toward an ocular dual muscle clamp. The clamp has a handle that consists of separable halves joined together at a spring loaded end. Projecting forwardly of each half of the handle is a fork-like member. Each fork-like member defines one half of a dual jaw mechanism. Accordingly, both fork-like members cooperate to define two pairs of jaws that work in unison between closed and released positions. A pre-loaded spring urges the jaws toward a normal released position. Therefore, the jaws must be subjected to an external manual force to close them to a clamping position. There is a latching mechanism for releasably latching the jaws in the clamping position.

The handle of the dual muscle clamp is cylindrical. A forward end of the cylindrical handle has a gripping section that is knurled. Rearwardly of the gripping section, the handle has the aforesaid pre-loaded spring. The overall length of the handle including the gripping section and the pre-sprung end is such that, with the gripping section held within the thumb and first two fingers of the hand, the rearward end, or spring end, projects far enough to rest against the hypothenar space of the hand.

DESCRIPTION OF THE PREFERRED EMBODIMENT

Figure 1:
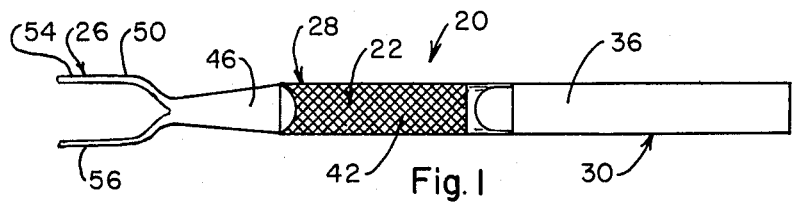
FIG. 1 is a top plan view of the dual muscle clamp.
Figure 2:
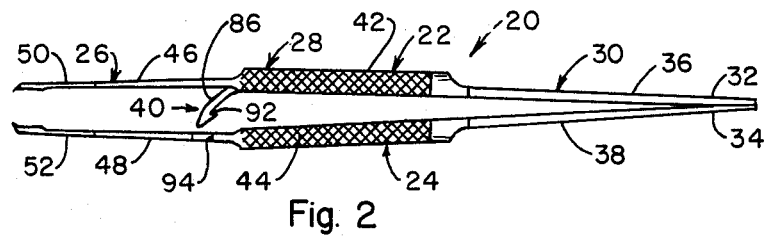
FIG. 2 is a right side elevation view of the dual muscle clamp in open condition.
Figure 4:
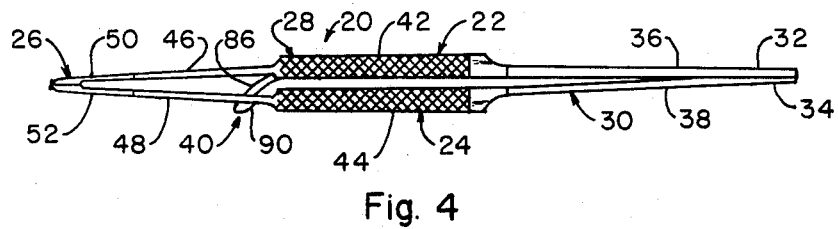
FIG. 4 is a right side elevation view of the dual muscle clamp in clamping condition.
Figure 5:
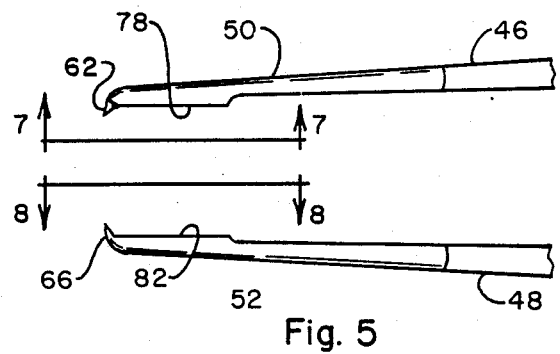
FIG. 5 is an enlarged partial side view of the jaws of the muscle clamp shown in open condition.
Figure 6:
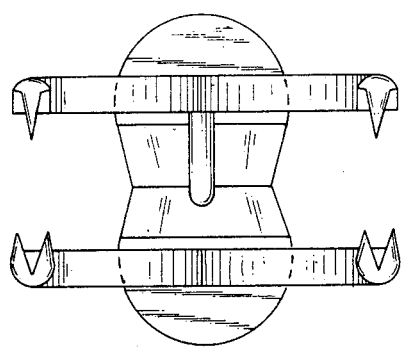
FIG. 6 is an enlarged left end view of the muscle clamp of FIG. 2.

The muscle clamp 20 of this invention is preferably formed primarily as two complementary body components 22 and 24 that cooperate to provide a clamping forward end 26, a central gripping section 28, and a rearward spring section 30. The two body components 22 and 24 are joined together at the back ends 32 and 34 thereof respectively. Forward of these back ends 32 and 34, the spring section 30 comprises two leaf springs 36 and 38. These back ends 32 and 34 are thickened and cooperate with the natural bias of the leaf springs 36 and 38 to hold the body components 22 and 24 in the spaced positions relative to one another as shown in FIG. 2. An external force can squeeze the body elements 22 and 24 together to the positions shown in FIG. 4, but when the external force is released, the springs 36 and 38 will return the body components 22 and 24 to the normal spread positions shown in FIG. 2. A latching mechanism 40 releasably locks the body components together in the clamping positions illustrated in FIG. 4 as will be further described.

The handle section 28 comprises a semi-cylinder 42 formed on the body component 22 and a complementary semi-cylinder 44 formed on the other body component 24. These semi-cylinders are about two inches long and about $\frac{3}{8}$ inch in diameter when pressed together to define a cylinder.

The clamping forward end 26 comprises a pair of flattened arms 46 and 48 extending forwardly of the semi-cylindrical handle sections 42 and 44. These arms 46 and 48 lead to opposed bifurcated jaw elements 50 and 52, respectively. The jaw element 50 thus is formed with a pair of parallel prongs 54 and 56 projecting forwardly from the arm 46, and the jaw element 52 is formed with a pair of parallel prongs 58 and 60 projecting forwardly of the arm 48.

The prongs 54 and 56 have individual inwardly and slightly forwardly projecting sharp points 62 and 64. The prongs 58 and 60 have inwardly and forwardly projecting pairs of sharp points 66 and 68 (on the prong 58) and 70 and 72 (on the prong 60). The points 66 and 68 define a groove 74 between them that extends across the forward end of the prong 58, and there is a similar groove 76 between the points 70 and 72. Therefore, although the points 66, 68, 70 and 72 are slightly forward of the points 62 and 64, the teeth 62 and 64 are aligned to fit within the grooves 74 and 76 when the body components 22 and 24 are squeezed together.

Figure 11:
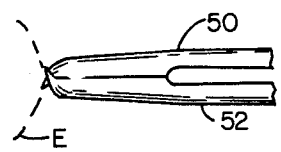
FIG. 11 is an enlarged partial side elevation view of the muscle clamp in the fully closed clamping condition.
Figure 7:
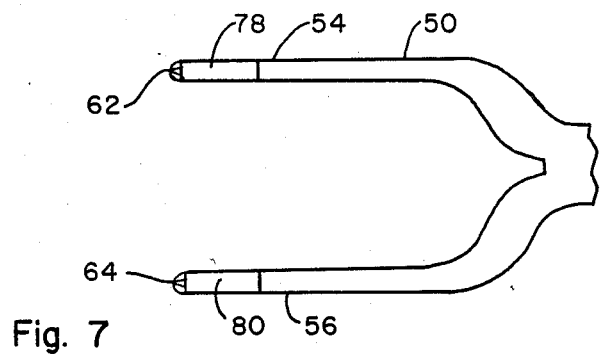
FIG. 7 is a partial view of the forward portion of one side of the muscle clamp generally as viewed along the line 7—7 of FIG. 5.
Figure 8:
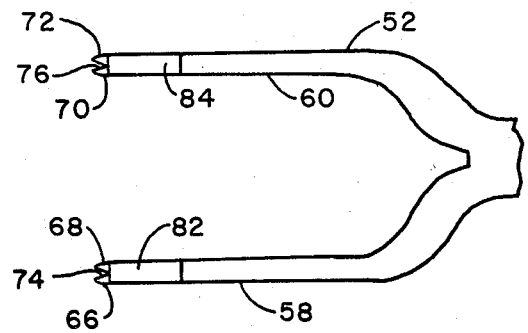
FIG. 8 is a partial view of the forward portion of the other side of the muscle clamp generally as viewed along the line 8—8 of FIG. 5.

Just rearward of the points that have just been described, there are flat seats 78 and 80 on the prongs 54 and 56, and oppositely facing seats 82 and 84 on the prongs 58 and 60. When the body components 22 and 24 are squeezed together, the seats 78 and 80 contact the seats 82 and 84, respectively, and establish the limits of intersection of the teeth 62 and 64 with the teeth 66, 68, 70 and 72 (see FIG. 11).

The latching mechanism 40 comprises a hook 86 secured to the inner side of one of the body component 22 and an opening 88 through the other body component large enough to receive the hook 86 through it.

The hook has a cam face 90 and a seat 92. The opening 88 has an actuating edge 94 (See FIG. 2). The hook 86 is spring biased to the position shown in FIG. 2 at which the cam face 90 is opposite the edge 94 of the opening 88. Therefore, to latch the muscle clamp in clamping condition, the body components 22 and 24 are squeezed toward one another at which time the cam face 90 contacts the edge 94 of the opening 88. This biases the hook 86 forwardly until, as the body components 22 and 24 are squeezed further together, the face 90 passes the edge 94 and the hook 86 snaps to the right (as viewed in FIGS. 2 and 4) pushing the seat 92 past the edge 94 into contact with the arm 48. This puts the mechanism 40 in clamping condition, holding the body components 22 and 24 in the clamped positions shown in FIG. 4. To release the clamping mechanism 40, the cam face 90 is pushed manually forward, by a thumb or finger, until the face 92 is forward of the edge 94. Then, the natural bias of the leaf springs 36 and 38 spreads the body components 22 and 24 back to the positions shown in FIG. 2.

This muscle clamp is preferably made of stainless steel. It weighs slightly less than one ounce. Its length from the forward end of the handle section 28 to the rearward end of the spring section 30 is preferably about $3\frac{1}{4}$ inches, enough to allow the cylindrical handle section 28 to be held between the thumb and fingers of a hand with the rear portion of the spring section 30 resting on the hypothenar space of the hand.

Figure 3:
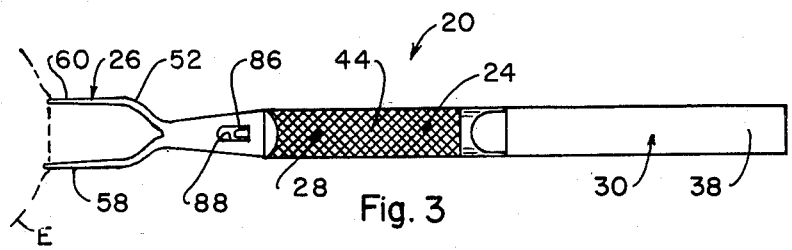
FIG. 3 is a bottom view of the dual muscle clamp showing the muscle clamp in closed clamping position.

In use, the muscle clamp 20 is typically held with the gripping section between the thumb and one or two fingers. An eye E, as diagramatically illustrated in FIG. 3, is to be clamped and held. Typically, the schlera of the eye is clamped on opposite sides of the area from which the surgeon has just severed an eye muscle. Once clamped, the eye is moved and held in the exact position required to enable re-attaching the muscle to the schlera at the new location.

Figure 9:
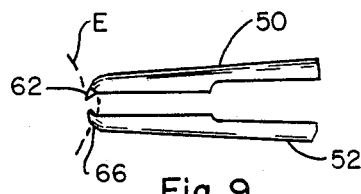
FIG. 9 is an enlarged partial side elevation view of the muscle clamp showing the muscle clamp initiating a clamping condition.
Figure 12:
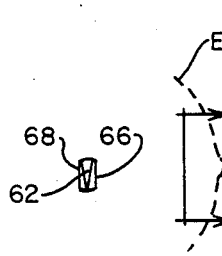
FIG. 12 is an enlarged front elevation view of one pair of prongs, shown clamped together generally as viewed along the line 12—12 of FIG. 10.
Figure 10:
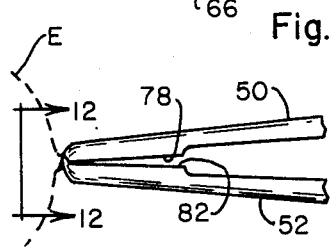
FIG. 10 is an enlarged partial elevation view of the muscle clamp squeezed further toward clamping condition.

When the forward ends of the prongs 54, 56, 58 and 60 are touching or close to touching the schlera on opposite sides of the specific area to be clamped, squeezing pressure is applied to the gripping sections 42 and 44. At the desired spots, the points 62 and 64 on one side and the points 66, 68, 70 and 72 on the other side pierce the schlera. This condition is illustrated in FIG. 9. Further squeezing of the gripping sections 42 and 44 brings the faces 78 and 80 into initial contact with the faces 82 and 84, respectively. At the same time, the teeth 62 and 64 will have slid into the spaces 74 and 76, as indicated in FIG. 12, but will have reached the limits of their travel because of the initial contact between the faces 78, 80 and 82, 84. Further squeezing of the gripping sections 42 and 44 causes the face 92 of the hook 86 to clear the opening 88, and the hook 86 snaps rearwardly to latch the body elements 22 and 24 together. Now, the faces 78 and 80 may be in full contact with the faces 82 and 84, but their initial contact will have prevented the points from moving any closer together.

All of the foregoing clamping action will have been accomplished with just one hand holding and controlling the dual muscle clamp 20, and will have taken place rapidly once the area to be clamped is specifically located. Now the surgeon, with one hand holding the handle section 28, can rotate and move the eye E to precisely the location and orientation he wants. Since the muscle clamp 20 clamps the eye E at two spaced locations, movements of the eye E can be controlled accurately by the muscle clamp 20.

When clamping is no longer needed, the latching mechanism 40 is released in the manner previously described and the body components 22 and 24 are allowed to separate under the force of the spring section 30. The points 62 and 64 and 66, 68, 70 and 72 release the schlera, and therefore the eye is released.

This dual muscle clamp fulfills the need, objects and advantages set forth. While the preferred embodiment has been described heretofore, this invention encompasses all modifications, variations, and uses as may be covered by the following claims.

What is claimed is:

1. An ocular muscle clamp for gripping an eyeball at spaced locations about its periphery, said clamp comprising first and second handle members, each handle member having a forward end and a rearward end;

means connecting said first and second handle members adjacent the rearward ends thereof to enable relative movement of said handle members toward each other and away from each other, said connecting means normally biasing said handle elements away from each other;

first and second U-shaped portions fixed to the respective forward ends of said first and second handle members, each of said U-shaped portions including spaced, elongated first and second legs, each of said first and second legs extending longitudinally in a forward direction and being spaced apart relative to each other so as to be able to contact an eyeball at spaced locations on the periphery thereof, the first and second legs of said first U-shaped portion being positioned in opposed relation respectively to the first and second legs of said second U-shaped portion, said first legs of each of said U-shaped portions defining a first opposed pair of legs and said second legs of each of said U-shaped portions defining a second opposed pair of legs; and tissue piercing means fixed adjacent to a forward end of at least one leg of each of said opposed pairs of legs and spaced from said handle member, said tissue piercing means including at least one pointed element constructed to pierce tissue of the eyeball, each of said pointed elements projecting generally fowardly from the leg to which said pointed element is fixed and toward the other leg of the respective opposed pair of legs, said pointed element on said one leg of each pair of opposed legs cooperating with the other leg of the respective opposed pair to grip eyeball tissue therebetween when said first and second handle members are moved toward each other and positioned together thereby gripping eyeball tissue at spaced locations about the periphery of the eyeball.

2. The ocular muscle clamp of claim 1 further including releasable latching means to latch said forward ends of said first and second handle members together with said tissue piercing means and the forward ends of said opposed pairs of legs in the tissue gripping position.

3. The ocular muscle clamp of claim 2 wherein said latching means comprise an opening in one of said handle members and a resilient hook member fixed on the other handle member, said hook element being movable through said opening to engage said one handle element and being movable to a position out of engagement with said one handle member to enable the handle members to move apart.

4. The ocular muscle clamp of claim 1 wherein said first and second U-shaped portions are integrally formed on the respective forward ends of said first and second handle members.

5. The ocular muscle clamp of claim 1 further including another tissue piercing means fixed adjacent to the forward end of the other leg of each opposed pair of legs, said other tissue piercing means including a pair of spaced pointed elements adapted to pierce tissue of the eyeball, said pair of spaced pointed elements projecting generally forwardly from the respective other legs and toward the forward end of said one leg of said opposed pair, said single pointed element on said one leg of each opposed pair adapted to be moved into the space between said spaced pointed elements on said other leg of each opposed pair such that eyeball tissue is gripped between said single pointed element and the respective pair of spaced pointed elements when the first and second leg members are moved toward each other and together.

6. The ocular muscle clamp of claim 1 further including stop means for limiting the movement of said handle members toward each other, said stop means being positioned adjacent the forward end of at least one leg of each of said opposed pairs of legs for contacting the other leg of each opposed pair.

7. The ocular muscle clamp of claim 1 wherein each of said first and second handle members includes a gripping portion having a semi-cylindrical outer periphery and a flat face inwardly of said outer periphery, said flat face on said gripping portion of said first handle member facing the flat face on the gripping portion of said second handle member whereby when the handle members are moved together said semi-cylindrical outer peripheries of said gripping portions define a substantially cylindrical gripping section.

8. An ocular muscle clamp for gripping the tissue of an eyeball at spaced locations on the periphery thereof, said clamp comprising opposed first and second clamping members, means connecting said first and second clamping members at one of the respective opposed ends thereof and enabling relative movement of said clamping members toward each other and away from each other, said connecting means normally biasing said clamping members away from each other, each of said first and second clamping members including discrete first and second substantially parallel elongated gripping portions extending from the clamping members opposite said connection means, each of said gripping portions having a free end, the first and second gripping portions of said first clamping member being positioned in opposed relation respectively to the first and second gripping portions of said second clamping member, said first gripping portions of the respective clamping members defining one opposed pair of gripping portions, said second gripping portions of the respective clamping members defining another opposed pair of gripping portions, each opposed pair of gripping portions including means to pinch eyeball tissue only at spaced discrete locations each opposed pair of gripping portions come into contact with tissue at the periphery of the eyeball when said first and second clamping members are moved toward each other.

9. The ocular muscle clamp of claim 8 further including latching means associated with the respective first and second clamping members and adapted to latch the first and second clamping members together to grip eyeball tissue between the gripping portions thereof.

10. An ocular muscle clamp for gripping an eyeball at spaced locations on the periphery thereof, said clamp comprising first and second handle members, said first and second handle members each having a forward end portion and a rearward end portion, means connecting said first and second handle members at the reearward end portions thereof and enabling relative movement of said handle members toward each other and away from each other, said connecting means normally biasing said handle members away from each other, the forward end portions of said first and second handle members being bifurcated to provide spaced apart, substantially parallel elongated first and second jaw members, each of said jaw members having a free end, the first and second jaw members of said first handle member being positioned in opposed relation respectively to the first and second jaw members of said second handle member, said first jaw members of the respective handle members defining one opposed pair of jaw members, said second jaw members of the respective handle members defining another opposed pair of jaw members, one jaw member of each opposed pair having a tissue piercing element projecting from adjacent the free end thereof in a direction generally toward the other jaw member of said opposed pair and adapted to pierce eyeball tissue, the other jaw member of each opposed pair having at least two tissue piercing elements projecting from adjacent the free end thereof in a direction generally toward the respective one jaw member and adapted to pierce eyeball tissue, said two tissue piercing elements defining a space therebetween, the tissue piercing element on said one jaw member adapted to be moved into the space between the two tissue piercing elements on said other jaw member of each opposed pair such that when the free ends of the jaw members of said opposed pairs are positioned in contact with the periphery of an eyeball and said first and second handle members are moved toward each other the tissue piercing element on the one jaw member and the two tissue piercing elements on the other jaw member of each opposed pair pierce the eyeball tissue and cooperate to grip the eyeball therebetween.

11. The ocular muscle clamp of claim 10 further including releasable latching means that can latch the first and second handle members together to grip eyeball tissue therebetween.

12. The ocular muscle clamp of claim 10 further including stop means located on at least one jaw member of each opposed pair between the free end of the jaw member and the rearward end portion of the respective handle member, said stop means limiting the relative movement of said first and second handle members toward each other.

* * * * *

UNITED STATES PATENT OFFICE
CERTIFICATE OF CORRECTION

Patent No. 4,610,252       Dated September 9, 1986

Inventor(s) J. Denis Catalano

It is certified that error appears in the above-identified patent and that said Letters Patent are hereby corrected as shown below:

Column 5, line 46, "fowardly" should be --forwardly--.

Column 7, line 6, "reearward" should be --rearward--.

Signed and Sealed this
Eleventh Day of November, 1986

*Attest:*

DONALD J. QUIGG

*Attesting Officer*     *Commissioner of Patents and Trademarks*